(12) United States Patent
Lian et al.

(10) Patent No.: US 10,583,296 B2
(45) Date of Patent: Mar. 10, 2020

(54) IMPLANTABLE PULSE GENERATOR SYSTEM AND METHOD FOR VAGAL NERVE STIMULATION

(71) Applicant: BIOTRONIK SE & Co. KG, Berlin (DE)

(72) Inventors: Jie Lian, Beaverton, OR (US); Lauren Kraiter, Tigard, OR (US); Andrew B. Kibler, Lake Oswego, OR (US)

(73) Assignee: BIOTRONIK SE & CO. KG, Berlin (DE)

( * ) Notice: Subject to any disclaimer, the term of this patent is extended or adjusted under 35 U.S.C. 154(b) by 113 days.

(21) Appl. No.: 15/489,829

(22) Filed: Apr. 18, 2017

(65) Prior Publication Data

US 2017/0304628 A1    Oct. 26, 2017

Related U.S. Application Data

(60) Provisional application No. 62/327,455, filed on Apr. 26, 2016.

(51) Int. Cl.
*A61N 1/36* (2006.01)

(52) U.S. Cl.
CPC ....... *A61N 1/36139* (2013.01); *A61N 1/3615* (2013.01); *A61N 1/36053* (2013.01); *A61N 1/36114* (2013.01); *A61N 1/36171* (2013.01); *A61N 1/36175* (2013.01)

(58) Field of Classification Search
None
See application file for complete search history.

(56) References Cited

U.S. PATENT DOCUMENTS

| 6,473,644 B1 | 10/2002 | Terry, Jr. |
| 7,778,703 B2 | 8/2010 | Gross et al. |
| 7,783,362 B2 | 8/2010 | Whitehurst et al. |

(Continued)

FOREIGN PATENT DOCUMENTS

| EP | 2 021 070 A2 | 2/2009 |
| EP | 2 813 262 A1 | 12/2014 |
| WO | WO 2013/086175 A1 | 6/2013 |

OTHER PUBLICATIONS

European Search Report, 17167503.6-1666, dated Jul. 25, 2017.

(Continued)

*Primary Examiner* — Erica S Lee
(74) *Attorney, Agent, or Firm* — Craig Fieschko; DeWitt LLP (57) ABSTRACT

An implantable pulse generator system includes a nerve stimulation unit providing vagal nerve stimulation (VNS) pulses; an autonomic tone sensor which determines the patient's autonomic status; and a control unit connected to the nerve stimulation unit and the autonomic tone sensor. The control unit controls the nerve stimulation unit to generate VNS with varying intensity, depending on the autonomic status (which is evaluated in a moving window). The control unit gradually increases VNS intensity when the autonomic status indicates a shift toward more sympathetic dominance, and it gradually decreases VNS intensity when the autonomic status indicates a shift toward more parasympathetic dominance, wherein the gradual increase and the gradual decrease of the VNS intensity follow two different paths.

16 Claims, 6 Drawing Sheets

(56) References Cited

U.S. PATENT DOCUMENTS

| | | |
|---|---|---|
| 8,401,604 B2 | 3/2013 | Gerlitz |
| 8,473,068 B2 | 6/2013 | Farazi |
| 8,712,547 B2 | 4/2014 | Whitehurst et al. |
| 2005/0076908 A1* | 4/2005 | Lee ................. A61B 5/0809 128/204.23 |
| 2007/0260285 A1 | 11/2007 | Libbus et al. |
| 2008/0058872 A1* | 3/2008 | Brockway .......... A61B 5/02405 607/2 |
| 2009/0281594 A1* | 11/2009 | King ................. A61N 1/36071 607/46 |
| 2010/0016921 A1* | 1/2010 | Campos ............ A61N 1/36021 607/48 |
| 2011/0301660 A1 | 12/2011 | Libbus et al. |
| 2013/0123873 A1 | 5/2013 | Libbus et al. |
| 2013/0158617 A1 | 6/2013 | Libbus et al. |
| 2013/0184773 A1 | 7/2013 | Libbus et al. |
| 2014/0114370 A1 | 4/2014 | Libbus et al. |
| 2014/0155949 A1 | 6/2014 | Libbus et al. |
| 2014/0371811 A1 | 12/2014 | Lian et al. |
| 2015/0182750 A1 | 7/2015 | Libbus et al. |
| 2016/0325100 A1 | 11/2016 | Lian et al. |

OTHER PUBLICATIONS

Henning, Robert J. et al. "Vagal nerve stimulation increases right ventricular contraction and relaxation and heart rate", Cardiovascular Research 32, 1996, 846-853.

* cited by examiner

IMPLANTABLE PULSE GENERATOR SYSTEM AND METHOD FOR VAGAL NERVE STIMULATION

CROSS-REFERENCE TO RELATED APPLICATIONS

This application claims priority under 35 USC § 119(e) to U.S. Provisional Patent Application 62/327,455 filed 26 Apr. 2016, the entirety of which is incorporated by reference herein.

FIELD OF THE INVENTION

This document concerns an invention relating generally to an implantable pulse generator system and a method for autonomic adaptive control of vagal nerve stimulation (VNS).

BACKGROUND OF THE INVENTION

Vagal nerve stimulation (VNS) systems and methods are described, for example, in U.S. Pat. Nos. 7,778,703, 7,783,362, 8,401,604, 8,473,068, 8,712,547, U.S. Patent Appl'n. Publ'n. 2013/0184773 and U.S. Patent Appl'n. Publ'n. 2014/0155949, as well as in Robert J. Henning et al., "Vagal nerve stimulation increases right ventricular contraction and relaxation and heart rate," Cardiovascular Research 32, 1996, 846-853.

VNS is applied in dependence on a parameter indicating autonomic tone of the patient, for example the heart rate (HR). VNS is equivalent to stimulation of the parasympathetic system. Therefore, VNS is not desired when the HR is too low. Common VNS systems are configured in a way that stimulation stops when the HR sinks below a certain value.

U.S. Pat. No. 6,473,644 B1 describes methods for adjusting VNS stimulation frequency in dependence on the ventricular HR of the patient. A damped feedback loop with hysteresis is used, with the HR as the controlling parameter and VNS stimulation frequency as the output.

SUMMARY OF THE INVENTION

The invention seeks to provide an improved system and method for vagal nerve stimulation (VNS). A preferred version of the invention involves an implantable pulse generator system that includes a nerve stimulation unit for generating and delivery of vagal nerve stimulation pulses; at least one autonomic tone sensor for determining an autonomic status of the patient and generating an autonomic status signal representing autonomic status; and a control unit connected to the nerve stimulation unit and the autonomic tone sensor. The control unit is configured to control the nerve stimulation unit to generate vagal nerve stimulation pulse trains that are adapted to cause vagal nerve stimulation with varying intensity, depending on the autonomic status signal. The control unit is further configured to evaluate the autonomic status signal in a moving window, and thereby generate an evaluated autonomic status signal. The control unit is further configured to gradually increase the intensity of VNS when the evaluated autonomic status signal indicates an autonomic tone that is shifting toward more sympathetic dominance, and gradually decrease the intensity of VNS when the autonomic status signal indicates an autonomic tone that is shifting toward more parasympathetic dominance, wherein the gradual increase and the gradual decrease of the intensity of the VNS follow two different paths (e.g., two different curves).

Preferably, the autonomic status signal is one or more of the following signals:
(1) a delay from the beginning of an electrical QRS signal to a vibration pulse measured at the cervical level via an accelerometer attached or adjacent to a VNS cuff;
(2) QRS duration;
(3) P wave duration;
(4) heart sound (contraction-induced pressure waves); and
(5) intra-cardiac pressure.

Hysteresis control is introduced to VNS so that the intensity of VNS is modulated not only based on the present autonomic tone, but also based on its past history. Adaptive delay of VNS intensity modulation is further introduced as a means of closed-loop control of VNS in response to a transient change of the patient's autonomic tone.

By means of such an implantable pulse generator system, a device and method for VNS is provided that ensures physiological adaptation of the VNS therapy to the changing autonomic balance while maintaining maximum appropriate therapy levels.

The invention includes the insight that vagal nerve stimulation (VNS) may be associated with the risk of causing clinically significant cardiac suppression. VNS is therefore preferably activated at a higher heart rate and deactivated at a lower heart rate. However, simply turning on/off the VNS based on heart rate cutoff values is not optimal since it does not consider the physiological adaptation of the VNS therapy, and may result in withholding therapy unnecessarily. In addition, transient heart rate changes due to natural heart rate variability, or the influence of measurement noise in the heart rate sensing unit, may cause frequent and unnecessary modulation of VNS therapy.

In a preferred version, the autonomic status signal represents the instantaneous heart rate on a beat-to-beat basis, or the instantaneous atrio-ventricular conduction time, and the moving window includes a predetermined number of heart rate values or atrio-ventricular conduction time values.

Preferably, the control unit is further configured to generate the evaluated autonomic status signal based on the average of the heart rate values or the atrio-ventricular conduction time values in the moving window. Accordingly, the control unit is configured to generate a moving average of the autonomic status signal, and thus causes a time delay that results in hysteresis.

The control unit is preferably further configured to increase the intensity of the VNS in response to a decrease of the heart rate, or an increase of the atrio-ventricular conduction time, and to decrease the intensity of the VNS in response to an increase of the heart rate, or a decrease of the atrio-ventricular conduction time.

The control unit is preferably further configured to cause an increase or a decrease of VNS intensity only when the autonomic status signal or the evaluated autonomic status signal is within a predetermined range of values.

The implantable pulse generator preferably further includes an activity sensor for determining an exertion level of the patient and generating a metabolic demand signal representing metabolic demand. The control unit is connected to the activity sensor and the autonomic tone sensor and is configured to control the stimulation unit depending on both the metabolic demand signal and the autonomic status signal. Adaptive control of vagal nerve stimulation (VNS) delivery is provided by adapting the VNS to both the autonomic status and metabolic demand of the patient. The implantable pulse generator includes at least one activity sensor for measuring the patient's exertion level (metabolic demand) and at least one autonomic tone sensor for detecting the autonomic status of the patient.

Closed loop control of vagal nerve stimulation (VNS) is desired to maximize beneficial effects for heart failure treatment while minimizing the risk of severe sympathetic depression. On one hand, it is preferred to activate and/or enhance VNS intensity in order to lower a patient's resting sympathetic tone. On the other hand, it is important to limit and/or inhibit VNS in order to preserve an appropriate degree of sympathetic activation when the patient is engaging in physical or mental activities. Maintaining the optimal balance between VNS and patient's exertion level remains to be a technical challenge.

The control unit of the implantable pulse generator system is preferably adapted to control the stimulation unit to generate stimulation pulses having stimulation parameters that are configured to induce a VNS effect that is either an increase in vagal tone or an increase in sympathetic tone, depending on both the metabolic demand signal and the autonomic status signal.

Preferably, the control unit and the stimulation unit are adapted to alter the effect of VNS by adjusting stimulation parameters including one or more of amplitude, pulse width, and/or selection of stimulating electrodes.

The response of each electrode or stimulation parameter set can be determined by characterization prior to or during therapy, and the result of characterization can be applied to the automatic adaptive control disclosed herein. Accordingly, it is preferred if the control unit is programmable.

In an exemplary arrangement, if the activity sensor indicates a patient is at rest but the sympathetic tone is elevated, then VNS is activated or its intensity is increased in order to enhance the vagal tone to achieve autonomic balance. Additionally or alternatively, if the activity sensor indicates the patient is involved in exertion activities but the sympathetic tone is suppressed, then VNS is adapted to decrease vagal tone or enhance sympathetic tone so that the patient is supported in physical or mental activities without artificially induced limitations on exertion.

Preferably, the control unit is adapted to control the stimulation unit to generate stimulation pulses having stimulation parameters that are configured to induce an increase in vagal tone if the metabolic demand signal of the activity sensor indicates a low demand and the autonomic status signal of the autonomic tone sensor indicates that the sympathetic tone is elevated.

The control unit is preferably adapted to control the stimulation pulse unit to generate stimulation pulses having stimulation parameters that are configured to induce a decrease in vagal tone and/or an increase in sympathetic tone if the metabolic demand signal of the activity sensor indicates an elevated metabolic demand and the autonomic status signal of the autonomic tone sensor indicates that the sympathetic tone is suppressed.

The activity sensor for providing a metabolic demand signal preferably includes at least one of an accelerometer, a CLS sensor (Closed Loop Stimulation sensor), and/or a minute ventilation sensor. A CLS sensor can measure both physical and mental exertion of a patient.

The CLS sensor and/or the minute ventilation sensor preferably include or are connected to an impedance determination unit that is configured to determine an intracardiac and/or a transthoracic impedance. Transthoracic impedance can be evaluated to determine a tidal volume (minute volume) and a breathing rate (minute rate). Intracardiac impedance can be used to determine stroke volume, contractility, heart rate and further metrics of a heart.

The CLS sensor is preferably configured to determine a course of intracardiac impedance and to compare the course with a reference course, and/or to determine a maximum of the first derivative of the course of intracardiac impedance.

The autonomic tone sensor is preferably configured to process IEGM signals representing an intracardiac electrogram (IEGM), and to determine one or more of the following metrics from IEGM signals: intrinsic heart rate (HR), intrinsic atrioventricular (AV) conduction time, QRS duration, and/or P wave duration. Alternatively or additionally, the autonomic tone sensor may be configured to process heart sound signals that reflect contraction-induced pressure waves, intra-cardiac pressure, and/or an impedance signal reflecting myocardial contractility.

The autonomic tone sensor therefore measures a physiological signal that is known to be affected by the autonomic status. For example, the device can use IEGM sensing electrodes to measure the intrinsic heart rate (HR), which is directly modulated by the autonomic status of the patient. Elevated sympathetic tone leads to an increase in HR, and vice versa. As another example, the intrinsic AV conduction time is affected by the autonomic status of the patient. Elevated sympathetic tone is associated with decrease in intrinsic AV conduction time and vice versa. Another measure of autonomic tone could be achieved by measuring the delay from beginning of electrical QRS signal to a vibration pulse measured at the cervical level via an accelerometer attached or adjacent to a VNS cuff. Such a vibration pulse reflects a local change of blood pressure in a cervical blood vessel arising from myocardial contraction of the heart. The delay between the QRS signal and the vibration pulse is related to cardiac contractility. Other physiological parameters can also be measured for the evaluation of autonomic status, including but not limited to QRS duration, P wave duration, heart sound (contraction-induced pressure waves), intra-cardiac pressure, etc. The autonomic tone measure can be used to derive the current autonomic state relative to a previous autonomic state.

A natural contraction of a heart chamber can be detected by evaluating the electrical signals sensed by the sensing channels. In the sensed electrical signal, the depolarization of an atrium muscle tissue is manifested by the occurrence of a P-wave. Similarly, the depolarization of ventricular muscle tissue is manifested by the occurrence of a R-wave. The detection of a P-wave or a R-wave signifies the occurrence of intrinsic atrial (As) or ventricular (Vs) events, respectively. The AV-delay is the time period between an atrial event and a prescribed point of time of a ventricular event. The heart rate (HR) is inverse to the time period between consecutive ventricular events.

In a healthy heart, initiation of the cardiac cycle normally begins with depolarization of the sinoatrial (SA) node. This specialized structure is located in the upper portion of the right atrium wall and acts as a natural "pacemaker" of the heart. In a normal cardiac cycle and in response to the initiating SA depolarization, the right atrium contracts and forces the blood that has accumulated therein into the ventricle. The natural stimulus causing the right atrium to contract is conducted to right ventricle via the atrioventricular node (AV node) with a short, natural delay, the atrioventricular delay (AV-delay). Thus, a short time after the right atrial contraction (a time sufficient to allow the bulk of the blood in the right atrium to flow through the one-way valve into the right ventricle), the right ventricle contracts, forcing the blood out of the right ventricle to body tissue. A typical time interval between contraction of the right atrium and contraction of the right ventricle might be 60 ms; a typical time interval between contraction of the right ventricle and the next contraction of the right atrium might be 800 ms. Thus, it is a right atrial contraction (A), followed a relatively short time thereafter by a right ventricle contraction (V), followed a relatively long time thereafter by the next right atrial contraction, that produces the desired AV synchrony. Where AV synchrony exists, the heart functions very efficiently as a pump in delivering life-sustaining blood to body tissue; where AV synchrony is absent, the heart functions as an inefficient pump (largely because the right ventricle is contracting when it is not filled with blood).

Another aspect of the invention involves a method for vagal nerve stimulation, the method including the steps of determining an exertion level indicating metabolic demand; determining an autonomous status level; and delivering nerve stimulation pulses depending on both the determined exertion level and the autonomic status level.

Nerve stimulation pulses having stimulation parameters that are configured to induce an increase in vagal tone are preferably delivered if the metabolic demand signal of the activity sensor indicates a low demand, and the autonomic status signal of the autonomic tone sensor indicates that the sympathetic tone is elevated. Additionally or alternatively, nerve stimulation pulses having stimulation parameters that are configured to induce a decrease in vagal tone and/or an increase in sympathetic tone are preferably delivered if the metabolic demand signal of the activity sensor indicates an elevated metabolic demand and the autonomic status signal of the autonomic tone sensor indicates that the sympathetic tone is suppressed.

DETAILED DESCRIPTION OF EXEMPLARY VERSIONS OF THE INVENTION

Figure 1:
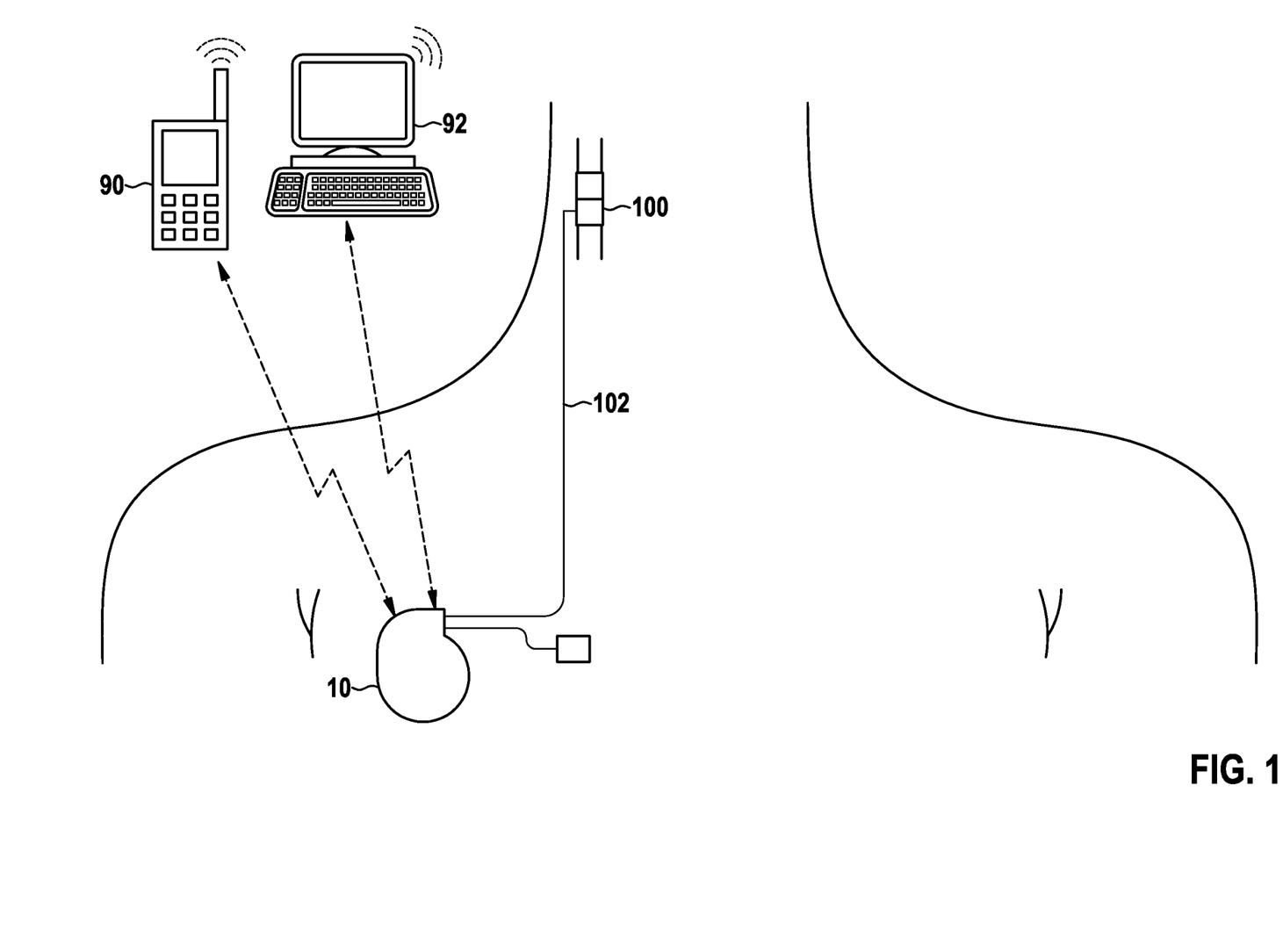
FIG. 1 shows an exemplary vagal nerve stimulation system.

FIG. 1 illustrates an implantable medical device 10, more particularly, an implantable pulse generator (IPG) for vagal nerve stimulation. The implantable medical device 10 is connected to a nerve stimulation electrode cuff 100 via a nerve stimulation electrode lead 102. The nerve stimulation lead 102 can optionally include one or more sensors for detecting cardiac signals, pressure signals or impedance signals.

The implantable pulse generator 10 can be wirelessly programmed by an external programmer 92 via a MICS-band or equivalent wireless communications link. The implantable pulse generator 10 can also communicate with a bedside Patient Messenger 90 via a similar wireless link. Arrhythmia detection, blood pressure waveform changes, and other relevant diagnostic parameters can be transmitted to the bedside Patient Messenger 90, which can alert a Home Monitoring/Remote Programming Center if the patient requires medical attention.

Figure 2:
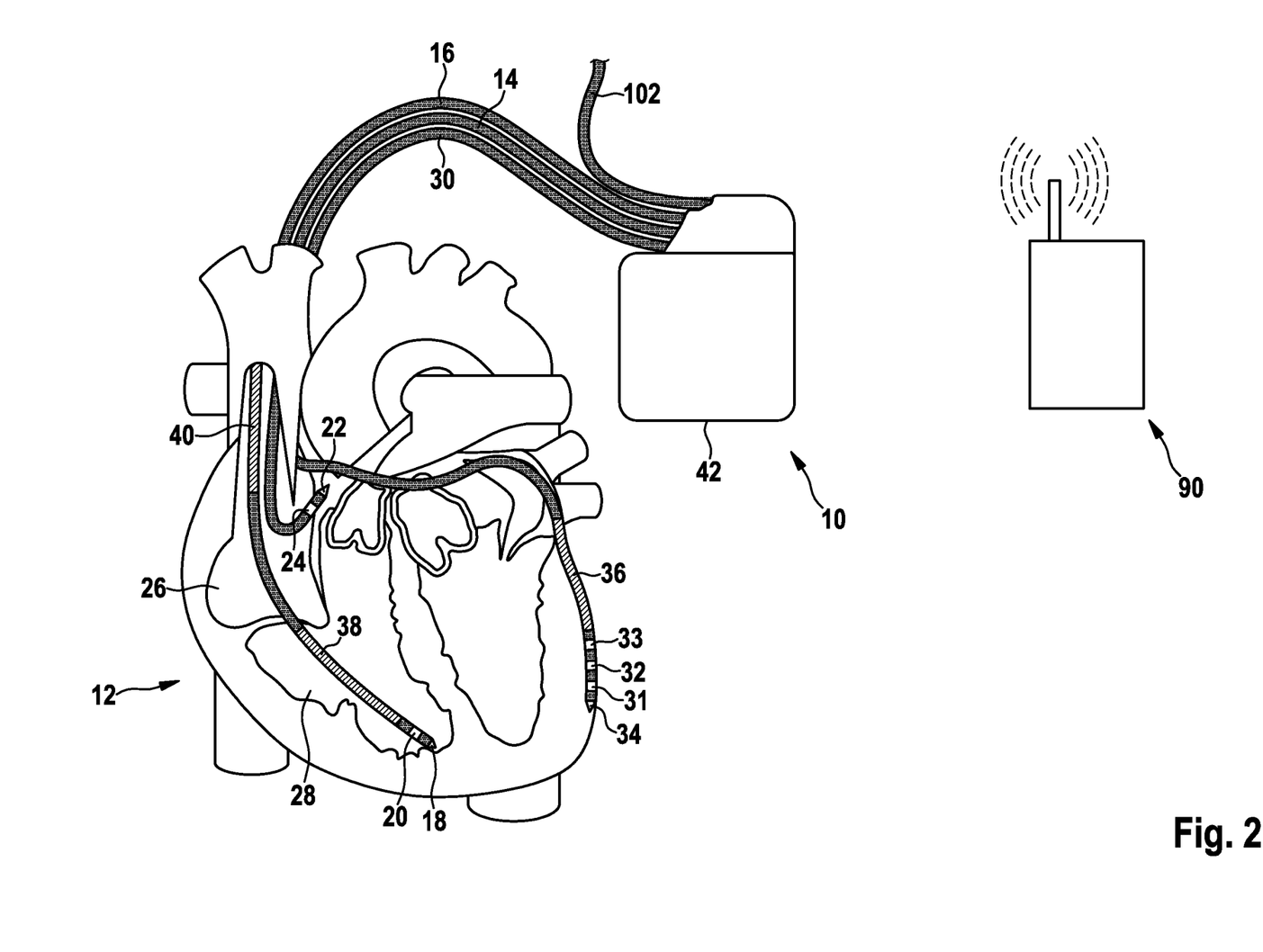
FIG. 2 illustrates an exemplary implantable pulse generator for heart stimulation and vagus stimulation.

FIG. 2 illustrates a preferred version of the implantable medical device 10 of FIG. 1, wherein the vagal nerve stimulation pulse generator is combined with a biventricular defibrillator. The implantable medical device 10 is connected to the cuff electrode 100 of FIG. 1 by means of the nerve stimulation electrode lead 102. The implantable medical device 10 also defines a three-chamber biventricular pacemaker and cardioverter/defibrillator, which is electrically coupled to the heart 12 by way of pacing/sensing leads 14, 16 and 30.

The lead 14 is a right atrial electrode lead having a pair of right atrial electrodes 22 and 24 in contact with the right atria 26 of the heart 12.

Lead 16 is a right ventricular electrode lead that has a pair of ventricular stimulation and sensing electrodes 18 and 20 in contact with the right ventricle 28 of the heart 12. A ventricular defibrillation shock coil 38 and an atrial defibrillation shock coil 40 are also provided on the lead 16.

Electrodes 22 and 18 are tip electrodes at the distal end of leads 14 and 16, respectively. Electrode 22 is a right atrial tip electrode (abbreviated RA Tip) and electrode 18 is a right ventricular tip electrode. Electrodes 24 and 20 are ring electrodes in close proximity to, but electrically isolated from, the respective tip electrodes 22 and 18. Electrode 24 forms a right atrial ring electrode (abbreviated RA Ring) and electrode 20 forms a right ventricular ring electrode (abbreviated RV Ring). Atrial cardioversion shock coil 40 is a coil electrode providing a relatively large geometric area when compared to the stimulation electrodes 18, 20, 22 and 24.

Lead 30 is a left ventricular electrode lead passing through the coronary sinus of heart 12 and having left ventricular ring (abbreviated LV Ring) electrodes 31, 32 and 33, a left ventricular tip (abbreviated LV Tip) electrode 34, and a left ventricular defibrillation shock coil 36. The number of left ventricular ring electrodes may vary, and where this document discusses any one of the left ventricular ring electrodes, the discussion should generally be regarded as applicable to any or all of them.

The implantable medical device 10 has a generator housing 42 made from electrically conductive material such as titanium that can serve as a large-surface electrode (abbreviated IMD Case).

The electrodes 18, 20, 22, 24, 31, 32, 33, 34, 36, 38 and 40 connected to the implantable medical device 10, together with the case 42, allow for a number of different electrode configurations for measuring intrathoracic and intracardiac impedance.

Figure 3:
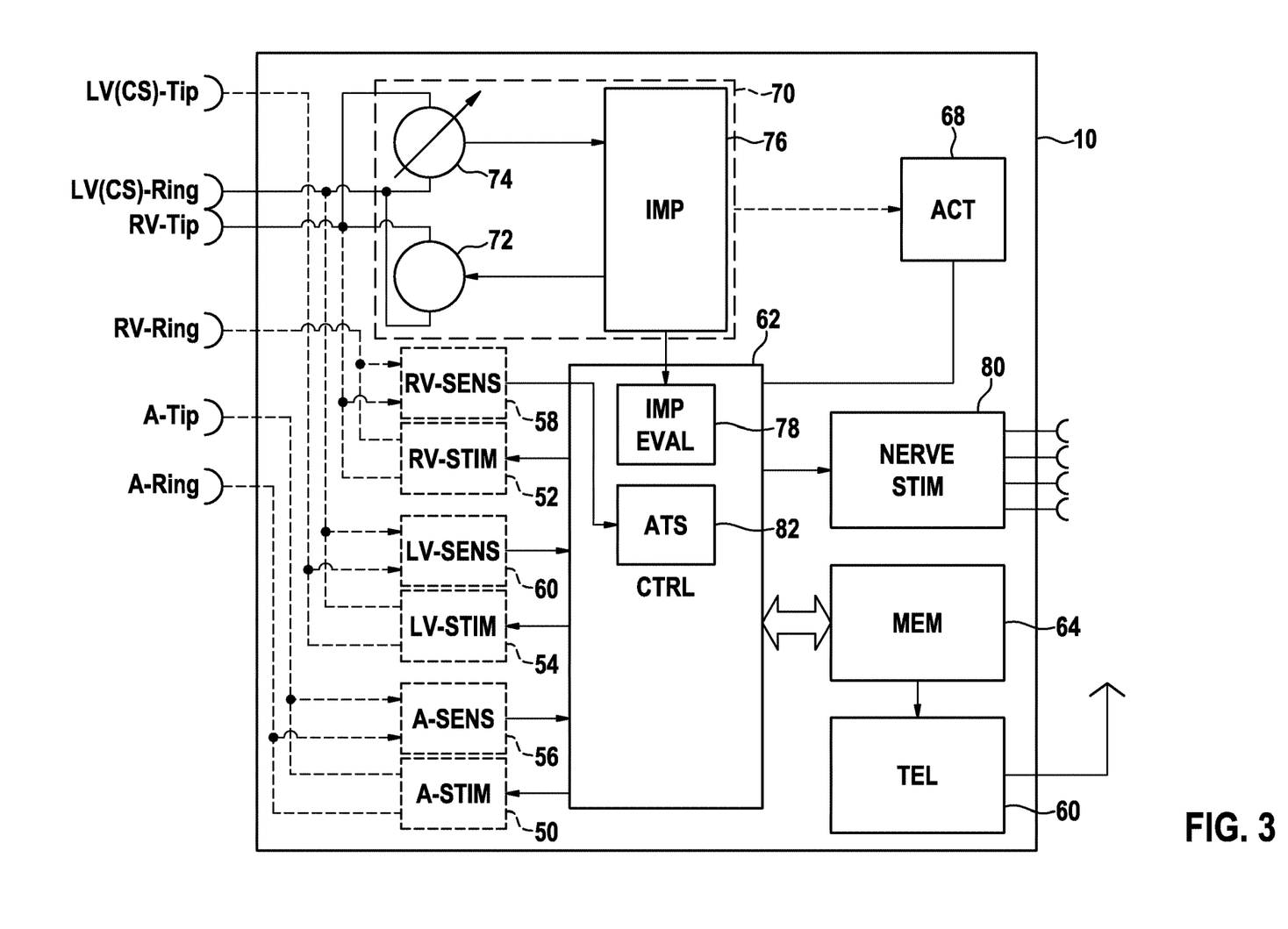
FIG. 3 is a schematic block diagram of an exemplary implantable pulse generator (IPG) suitable for use in the system of FIG. 1.
Figure 4:
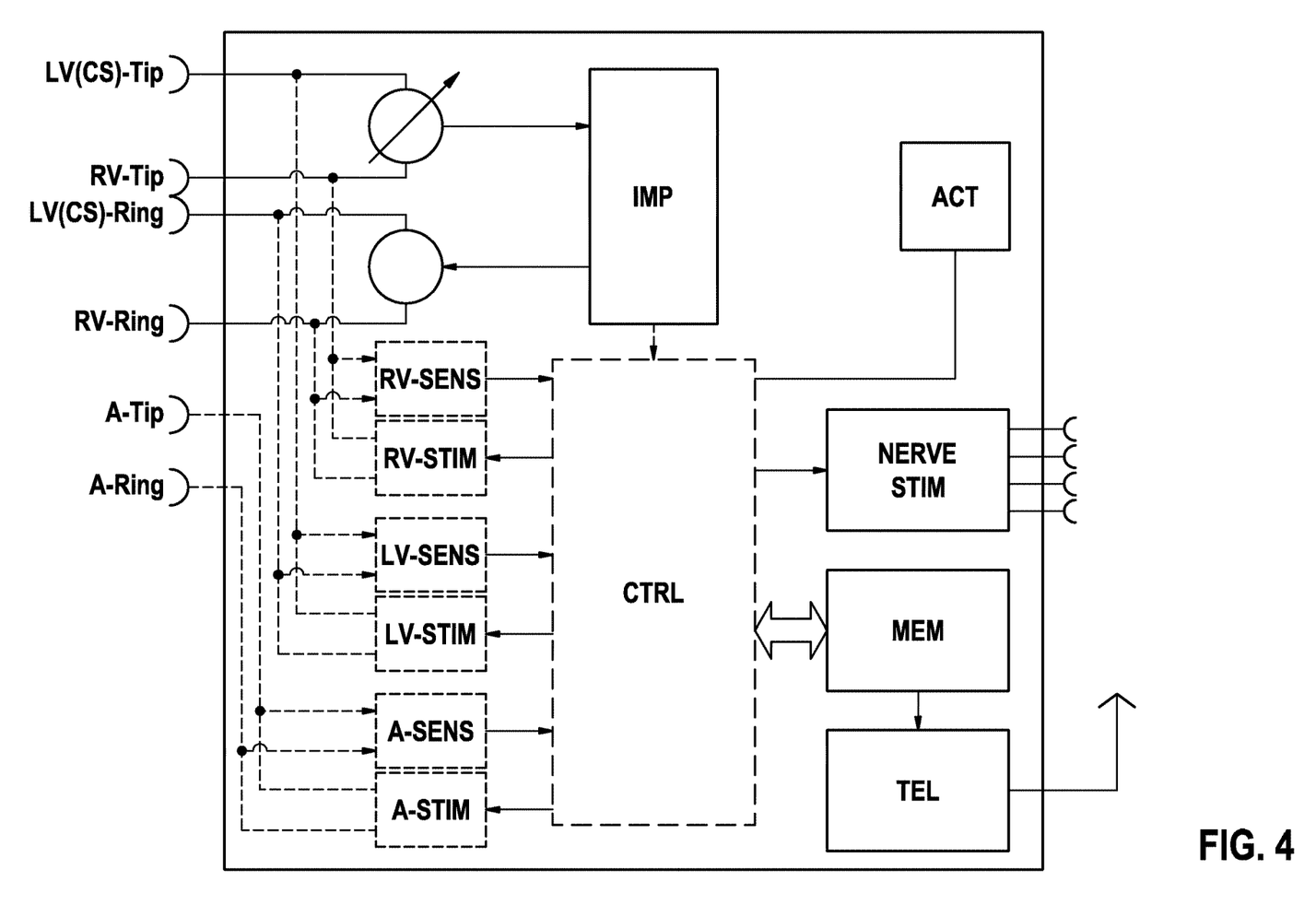
FIG. 4 is a schematic block diagram of an exemplary implantable pulse generator (IPG) suitable for use in the system of FIG. 1, showing an alternative electrode arrangement.

Each of the intracardiac impedance measurements can be made by injecting a forcing function from a right ventricular ring electrode to a left ventricular ring electrode and measuring a response function between the same electrodes (bipolar configuration, see FIG. 2); or between a right ventricular tip electrode and a left ventricular tip electrode (quadrupolar configuration, see FIG. 3). Alternative or additional impedance measurement vectors resulting from different impedance measurement electrode combinations are possible.

FIG. 3 depicts a simplified block diagram of an implantable medical device 10. During operation, leads 14, 16 and 30 are connected to respective output/input terminals of device 10 as indicated in FIG. 2, and carry stimulating pulses to the tip electrodes 18, 22 and 34 from a right atrial stimulation pulse generator A-STIM 50, a right ventricular pulse generator RV-STIM 52, and a left ventricular pulse generator LV-STIM 54. Further, electrical signals from the right atrium are carried through the lead 14 from the electrode pair 22 and 24 to the input terminal of a right atrial channel sensing stage A-SENS 56, and electrical signals from the right ventricle are carried through the lead 16 from the electrode pair 18 and 20 to the input terminal of a right ventricular sensing stage RV-SENS 58. Likewise, electrical signals from the left ventricle are carried through the lead 30 from the electrode pair 32 and 34 to the input terminal of a left ventricular sensing stage LV-SENS 60.

The implantable medical device 10 is controlled by a control unit CTRL 62 that is connected to sensing stages A-SENS 56, RV-SENS 58 and LV-SENS 60 and to stimulation pulse generators A-STIM 50, RV-STIM 52 and LV-STIM 54. Control unit CTRL 62 receives the output signals from the atrial sensing stage A-SENS 56, from the right ventricular sensing stage RV-SENS 58, and from the left ventricular sensing stage LV-SENS 60. The output signals of sensing stages A-SENS 56, RV-SENS 58, and LV-SENS 60 are generated each time that a P-wave representing an intrinsic atrial event or an R-wave representing an intrinsic ventricular event is sensed within the heart 12. An As-signal is generated when the atrial sensing stage A-SENS 56 detects a P-wave, and a RVs-signal is generated when the right ventricular sensing stage RV-SENS 58 detects an R-wave. These sense events are used by control unit CTRL 62 as fiducial points of the respective intracardiac electrograms picked up by the sensing stages A-SENS 56, RV-SENS 58, and LV-SENS 60.

Control unit CTRL 62 also generates trigger signals that are sent to the atrial stimulation pulse generator A-STIM 50, the right ventricular stimulation pulse generator RV-STIM 52, and the left ventricular stimulation pulse generator LV-STIM 54, respectively. These trigger signals are generated each time that a stimulation pulse is to be generated by the respective pulse generator A-STIM 50, RV-STIM 52 or LV-STIM 54. The atrial trigger signal is referred to as the "A-pulse", and the ventricular trigger signal is referred to as the "RV-pulse" or the "LV-pulse", respectively. During the time that either an atrial stimulation pulse or ventricular stimulation pulse is being delivered to the heart, the corresponding sensing stage, A-SENS 56, RV-SENS 58, and/or LV-SENS 60 is typically disabled by way of a blanking signal presented to these amplifiers from the control unit CTRL 62. This blanking action prevents the sensing stages A-SENS 56, RV-SENS 58, and LV-SENS 60 from becoming saturated from the relatively large stimulation pulses that are present at their input terminals during this time. This blanking action also helps prevent interpreting any residual electrical signals present in the muscle tissue (as a result of a stimulation pulse delivered from pacemaker 10) as P-waves or R-waves.

Furthermore, atrial sense events recorded shortly after delivery of a ventricular stimulation pulses, during a preset time interval called the post-ventricular atrial refractory period (PVARP), may be recorded as atrial refractory sense events Ars, but may be ignored.

Control unit CTRL 62 includes circuitry for timing ventricular and/or atrial stimulation pulses according to an adequate stimulation rate that can be adapted to a patient's hemodynamic need, as described further below.

Control unit CTRL 62 further includes an autonomic tone sensor 82 connected to the right ventricular sensing stage 58. The autonomic tone sensor 82 is configured to process IEGM signals representing an intracardiac electrogram (IEGM). The autonomic tone sensor 82 is preferably adapted to determine one or more of the following metrics from IEGM signals: intrinsic heart rate (HR), intrinsic atrioventricular (AV) conduction time, QRS duration, and/or P wave duration.

Still referring to FIG. 3, the implantable medical device 10 includes a memory circuit MEM 64 coupled to the control unit CTRL 62 over a suitable data/address bus ADR. This memory circuit MEM 64 allows certain control parameters, used by the control unit CTRL 62 for control of the operation of the implantable medical device 10, to be programmably stored and modified as required in order to customize the operation of the implantable medical device 10 to suit the needs of a particular patient. Such data includes the basic timing intervals used during operation of the pacemaker 10, in particular, AV delay values and hysteresis AV delay values.

Further, data sensed during the operation of the implantable medical device 10 may be stored in the memory MEM 64 for later retrieval and analysis.

The implantable medical device 10 also includes a telemetry circuit TEL 66 connected to the control unit CTRL 62 by way of a suitable command/data bus. Telemetry circuit TEL 66 allows for wireless data exchange between the implantable medical device 10 and a remote programming or analyzing device, including a remote device which is part of a centralized service center serving multiple pacemakers.

The implantable medical device 10 in FIG. 3 is referred to as a three chamber pacemaker/cardioverter/defibrillator because it interfaces with the right atrium 26, the right ventricle 28, and the left ventricle of the heart 12. Those portions of the pacemaker 10 that interface with the right atrium, e.g., the lead 14, the P-wave sensing stage A-SENSE 56, the atrial stimulation pulse generator A-STIM 50, and corresponding portions of the control unit CTRL 62, are commonly referred to as the atrial channel Similarly, those portions of the pacemaker 10 that interface with the right ventricle 28, e.g., the lead 16, the R-wave sensing stage RV-SENSE 58, the ventricular stimulation pulse generator RV-STIM 52, and corresponding portions of the control unit CTRL 62, are commonly referred to as the ventricular channel.

In order to be able to determine a patient's metabolic demand, the pacemaker 10 includes a physiological sensor (activity sensor) ACT 68 connected to the control unit CTRL 62 of the pacemaker 10. While this sensor ACT 68 is illustrated in FIG. 3 as being included within the pacemaker 10, the sensor 68 may instead be external to the implantable medical device 10, yet still be implanted within or carried by the patient. A common type of activity sensor is an accelerometer, such as a piezoelectric crystal, mounted to the case of the pacemaker 10. Other types of physiological/activity sensors are also known, such as sensors that sense the oxygen content of blood, respiration rate, blood pH, intracardiac impedance changes, and the like. The type of activity sensor used is not critical to the invention, and any sensor capable of sensing some physiological parameter relatable to physical activity and/or metabolic demand of a patient can be used. Such physiological sensors are commonly used with "rate-responsive" pacemakers in order to adjust the rate of the pacemaker in a manner that tracks the physiological needs of the patient. The output of sensor 68 represents an activity level.

In an exemplary version of the invention, the activity sensor 68 is an accelerometer. Alternatively, the activity sensor 68 may be a CLS sensor, which has been shown to be able to measure both physical and mental exertion of the patient. Another preferred alternative activity sensor 68 is a minute ventilation sensor, which utilizes measurements of trans-thoracic impedance signals.

Using the output signal of activity sensor 68, the control unit 62 is able to assign each intrinsic heart rates to activity levels, thereby enabling collection of intrinsic heart rate values for a patient's state of rest and a patient's state of exercise.

An impedance determination unit 70 is provided for impedance measurement. The impedance determination unit 70 includes a constant current source 72 connected to (or connectable to) electrodes for intracorporeal placement as shown in FIG. 1. To allow for different impedance measurement electrode configurations, some means of switching may be provided between the constant current source 72 and the electrode terminals of the implantable medical device 10. A switch arrangement is not shown in FIG. 2, and rather particular impedance measurement configurations are shown as examples.

Similarly, a voltage measuring unit 74 for measuring a voltage corresponding to a current fed through the body by the constant current source 72 is provided, and can be connected to a number of electrodes (though a switch for switching between these configurations is not shown in FIG. 2).

As an alternative to the constant current source 72, a constant voltage source can be provided to generate the forcing function. The measuring unit 74 is then adapted to measure a current strength fed through the body by the constant voltage source.

Both the constant current source 72 and the voltage measurement unit 74 are connected to an impedance value determination unit 76 that is adapted to determine an impedance value for each measuring current pulse delivered by the constant current source 72.

An evaluation unit 78, provided as part of control unit CTRL 62 (as depicted in FIG. 2) or as a separate unit, is connected to the impedance determination unit 70 and is adapted to evaluate a sequence of consecutive impedance values determined by the impedance determination unit 70. The evaluation unit 78 includes a signal generator module (not shown) to construct the intracardiac impedance or conductance signal reflecting the time course of the output signal of the impedance determination unit 70, and its derivative. The evaluation unit 78 further includes a filter module (not shown) to filter the intracardiac impedance signal.

The evaluation unit 78 is further connected to the right ventricular stimulation stage RV-STIM 52 and the right ventricular sensing stage RV-SENS 58 in order to receive signals representing cardiac events, namely right ventricular stimulation events RVp or right ventricular sense events RVs.

The constant current source 72 has its two poles connected to different connectors for different electrodes, for example the right ventricular ring electrode and the left ventricular ring electrode (FIG. 2) or the left ventricular tip electrode and the right ventricular tip electrode (FIG. 3). The voltage measuring unit 74 has two poles connected to, for example, a connector for the right ventricular ring electrode and the left ventricular ring electrode (FIG. 2) or the left ventricular ring electrode and the right ventricular ring electrode (FIG. 3). Thus, a bipolar or a quadrupolar impedance measurement configuration is established.

Impedance measurement is carried out by injecting a constant current and sampling the resulting voltage.

The measuring current is preferably pulsed. Typically, the measuring current will feature biphasic pulses wherein two constant current pulses of opposite polarity form one pulse package. A time gap is provided between each two consecutive pulse packages, with the time gap being significantly longer than the duration of one pulse package. The constant current pulses within one pulse package are each of the same intensity and of same duration, but having different polarities. As exemplary parameters, a constant current pulse may have an intensity between 50 µA and 600 µA, and a duration of about 15 µs.

The time gap between each two consecutive pulse packages may be 500 times longer than the duration of one constant current pulse. The two constant current pulses of opposite polarity within a pulse package may not immediately follow each other, but may have a time gap therebetween. However, this time gap will be very short compared to the time gap between two consecutive pulse packages. Furthermore, consecutive pulse packages may alternate phases, such that (for example) a first pulse package will begin with a positive constant current pulse followed by a negative constant current pulse, whereas the following pulse package will begin with a negative constant current pulse and end with a positive constant current pulse.

The control unit 62 is able to determine a stroke volume via intracardiac impedance measurement. The control unit 62 is also able to determine a tidal volume and a ventilation rate (breathing rate) via intrathoracic impedance measurement in a known manner.

The implantable pulse generator 10 further includes a nerve stimulation unit 80 for generating nerve stimulation pulses. The nerve stimulation unit 80 is connected to and controlled by the control unit 62. When in use, the nerve stimulation unit 80 is further connected to a nerve stimulation electrode lead, which is preferably a quadrupolar lead including four electric conductors connecting the nerve stimulation unit 80 to corresponding stimulation electrode poles of a nerve stimulation electrode cuff.

Hysteresis is an intrinsic behavior of cardiovascular system, respiratory system, and many other physiological systems. It regulates the normal function of the human body based on not only its current physiological status, but also its past history.

VNS is a known therapy to treat many diseases, including heart failure. However, overtreatment by VNS may be associated with the risk of severe sympathetic suppression, leading to side effects such as bradycardia. Simply turning on/off the VNS therapy based on a predefined heart rate cutoff value is not optimal because it does not consider adapting VNS to the past history of the patient's physiological status. Introducing hysteresis control to VNS may ensure more physiological adaptation of the VNS therapy to the changing autonomic tone.

According to this invention, the VNS system includes an autonomic tone sensing unit which measures a physiological signal that is known to be affected by the autonomic status. For example, the system can use IEGM sensing electrodes to measure the intrinsic heart rate (HR), which is directly modulated by the autonomic status of the patient. Elevated sympathetic tone leads to increase in HR and vice versa. As another example, the intrinsic AV conduction time is known to be affected by the patient's autonomic status. Elevated sympathetic tone is associated with decreased intrinsic AV conduction time and vice versa. Other physiological parameters can also be measured for the evaluation of autonomic status, including but not limited to QRS duration, P wave duration, heart sound, intracardiac pressure, minute ventilation, etc. In the following description, the HR is used as an example of autonomic tone indicator to illustrate the concept of the invention, but it should be understood that other and/or additional metrics can be used to measure the patient's autonomic tone.

Figure 5:
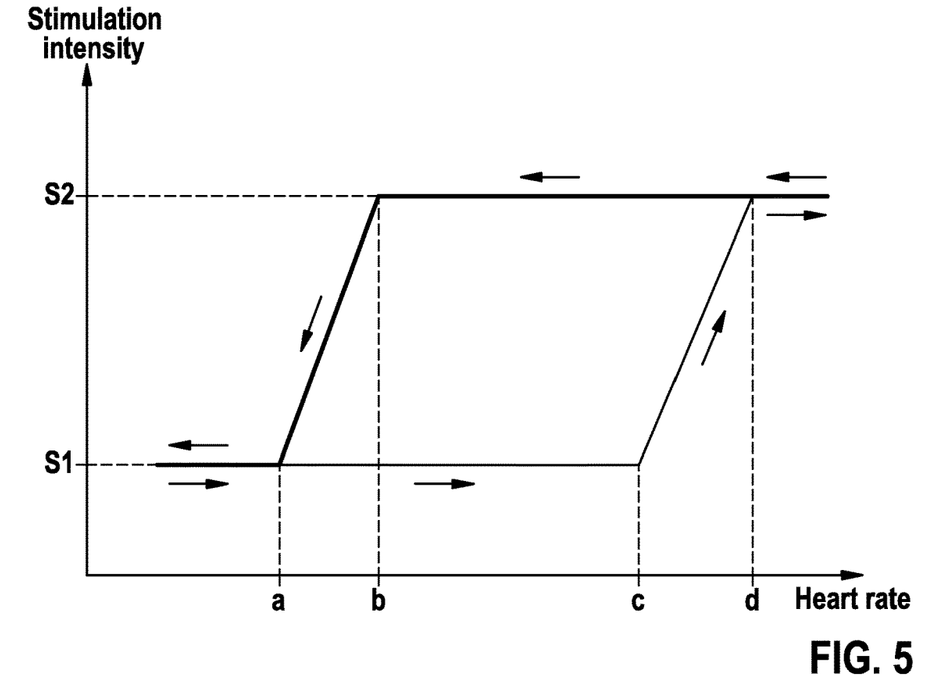
FIG. 5 is an illustration of an example of hysteresis control of VNS.
Figure 6:
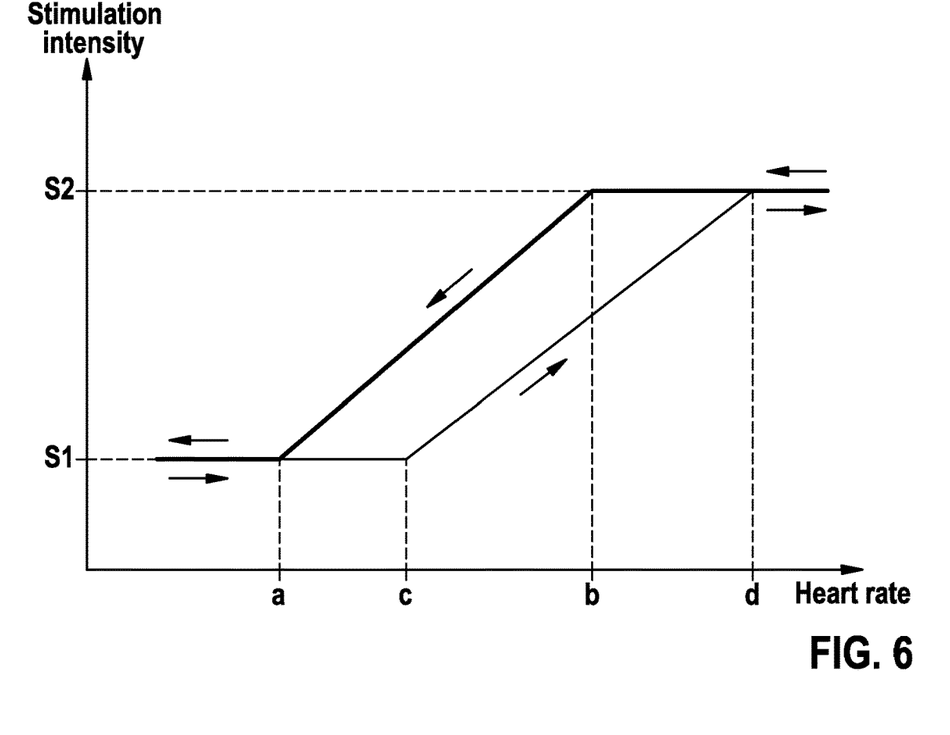
FIG. 6 is an illustration of another example of hysteresis control of VNS
Figure 7:
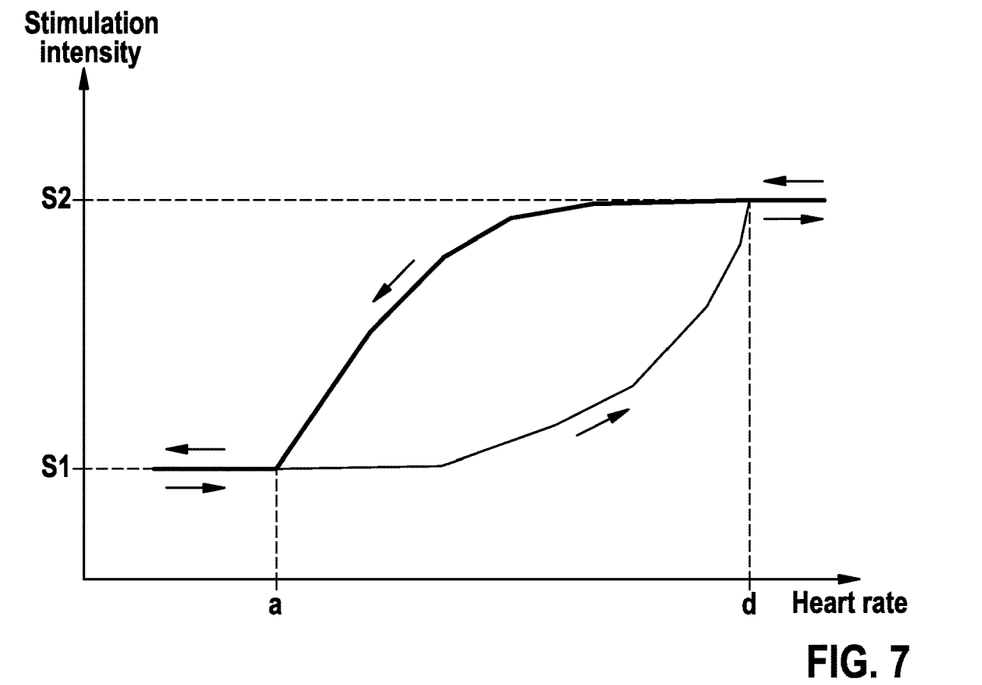
FIG. 7 illustrates an alternative means of hysteresis control of VNS.

In a preferred version of the invention, hysteresis is used to control VNS. Generally, within a predetermined range of autonomic tone (e.g., a predefined HR range), the intensity of VNS gradually increases when the sensed autonomic tone is shifting toward more sympathetic dominance (e.g., HR increase), and gradually decreases when the sensed autonomic tone is shifting toward more parasympathetic dominance (e.g., HR decrease). The increase and decrease of VNS intensity follow two different curves. At a specific autonomic tone within the predetermined range (e.g., a specific HR within the predefined HR range), the VNS intensity is higher if autonomic tone is shifting toward more parasympathetic dominance (e.g., HR decrease) than the VNS intensity would be if autonomic tone was shifting toward more sympathetic dominance (e.g., HR increase). FIGS. 5-7 illustrate three different examples of hysteresis control of VNS.

In FIG. 5, heart rates a, b, c and d define the hysteresis curves, where a<b<c<d, and these parameters are predefined or user-programmable. As HR increases, the intensity of vagal nerve stimulation does not increase until HR is higher than c, and reaches full intensity S2 when HR reaches d. As heart rate decreases, the intensity of VNS does not decrease until HR is lower than b, and reaches lowest intensity S1 when HR reaches a.

The example shown in FIG. 6 is similar to that in FIG. 5. Predefined or user-programmable heart rates a, b, c and d define the hysteresis curves, but HR b is greater than HR c (though heart rates b and c could be equal, i.e., b=c). As HR increases, the intensity of VNS does not increase until HR is higher than c, and reaches full intensity S2 when HR reaches d. As heart rate decreases, the intensity of vagal nerve stimulation does not decrease until HR is lower than b, and reaches lowest intensity S1 when HR reaches a.

In the example shown in FIG. 7, two heart rates a and d are predefined or user programmable, and a<d. The VNS remains at the lowest intensity S1 when HR is less than or equal to a. The VNS gradually increases toward S2 when HR is greater than a, but is less than d. Then when HR is greater than or equal to d, the VNS reaches the highest intensity S2.

In the foregoing examples, S1 and S2 are preferably user-programmable VNS parameters. As known in the art, the VNS intensity (including S1 and S2) can be controlled by programming stimulation amplitude, pulse width, pulse frequency, and/or other pulse timing such as duty cycling. S1 may be defined as VNS off (i.e., no VNS is delivered).

In an alternative version of the invention, modulation of VNS intensity is delayed in an adaptive manner in response to a transient change in the patient's autonomic tone. As described above, the patient's autonomic tone can be measured in a number of different ways. In the following discussion, the patient's heart rate is used as an indicator of the patient's autonomic tone, but it should be understood that other metrics could be used to measure the patient's autonomic tone.

Figure 8:
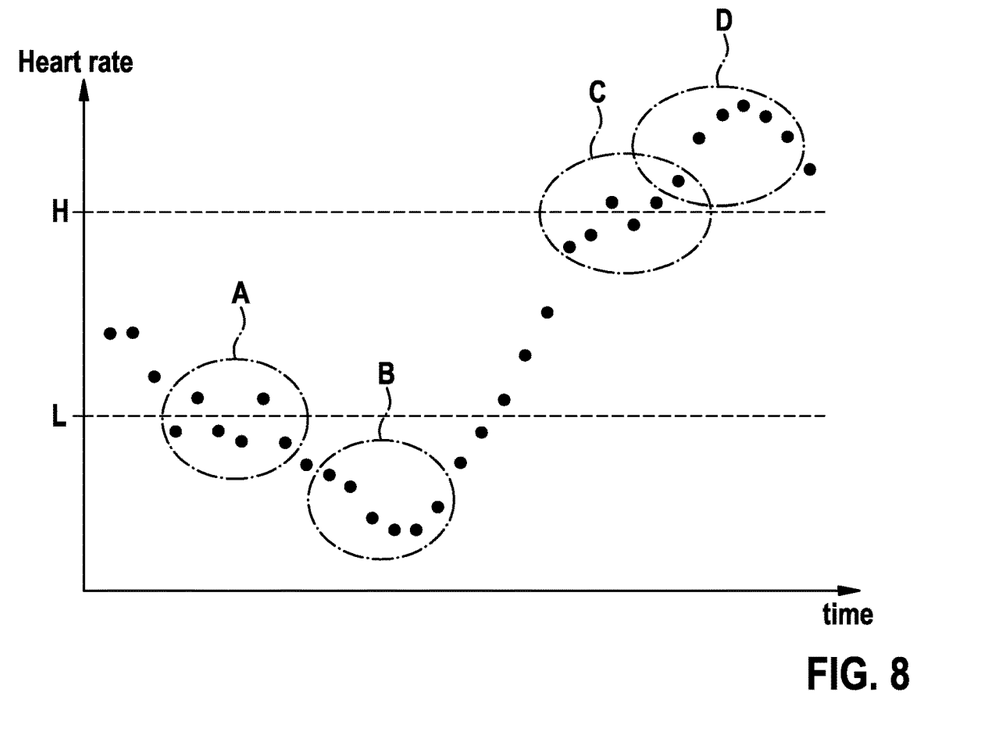
FIG. 8 is an illustration of adaptive delay for closed loop control of VNS in response to a transient change of a patient's heart rate tone.

As illustrated in FIG. 8, adaptive delay of VNS intensity modulation may be introduced as a means of closed-loop control of VNS in response to transient changes in the patient's heart rate (as an indicator of autonomic tone). In FIG. 8, each small circle represents an instantaneous heart rate measurement after one cardiac cycle. The VNS device continuously monitors the heart rate and evaluates the patient's autonomic tone based on the measured heart rate. The device also evaluates the severity of sympathetic elevation when the heart rate is persistently high, and the severity of vagal depression when the heart rate is persistently low. Based on such evaluations, the device further modulates the intensity of VNS therapy. Transient heart rate changes measured by the device due to (for example) natural heart rate variability or measurement noise is managed by means of an adaptive delay function as described below, to prevent the device from frequently and unnecessarily changing the intensity of VNS therapy.

In preferred version, at least one high heart rate limit and one low rate limit are predefined. This is exemplified by FIG. 8, wherein a high heart rate limit (H) and a low heart rate limit (L) are predefined. The device continuously measures the instantaneous heart rate and evaluates the severity of sympathetic elevation and the severity of vagal suppression in a moving window (with the size of the moving window being set to 6 cardiac cycles in FIG. 8). In an exemplary version, the severity of sympathetic elevation is quantitatively calculated as SSE=$\Sigma[R(i)-H]$, and the severity of vagal depression is quantitatively calculated as SVD=$\Sigma[L-R(i)]$, where i is the beat index, R(i) is the instantaneous heart rate at the i-th beat, and the summation is performed over all beats in the moving window. Therefore, a beat with instantaneous heart rate higher than H will increase SSE, while a beat's heart rate lower than H will decrease SSE. Similarly, a beat with instantaneous heart rate dropping below L will increase SVD, and a beat's heart rate higher than L will decrease SVD.

Preferably, when the calculated SSE exceeds a predefined sympathetic tone threshold (STH), VNS is modulated upward to increase the intensity of stimulation. On the other hand, when the calculated SVD exceeds a predefined vagal tone threshold (VTH), VNS is modulated downward to decrease the intensity of stimulation. Because the calculation of SSE and SVD is performed over a moving window, a transient heart rate decrease below L will be balanced by those beats above L (see A in FIG. 8), and will not necessarily trigger modulation of VNS therapy. Only when the heart rate is persistently below the target rate L, such that the calculated SVD exceeds the predefined VTH (see B in FIG. 8), will downward modulation of VNS be initiated. Similarly, a transient heart rate increase above H will be balanced by those beats below H (see C in FIG. 8), and therefore will not trigger modulation of VNS therapy. Upward modulation of VNS will be activated only when the heart rate is persistently above the target rate H, such that the calculated SSE exceeds the predefined STH (see D in FIG. 8).

It should be understood that the equations above used to calculate SSE and SVD are merely for the purpose of illustration, and other formulae can be developed to quantify SSE and SVD. For example, a set of predefined coefficients can be applied to the difference $[R(i)-H]$ for the calculation of SSE, while another set of predefined coefficients can be applied to the difference between $[L-R(i)]$ for the calculation of SVD, and these coefficients can be rate dependent as well. In another example, the difference terms $[R(i)-H]$ and $[L-R(i)]$ can be scaled nonlinearly. Yet in another example, the difference terms $[R(i)-H]$ and $[L-R(i)]$ can be respectively replaced by the evaluating the differences in duration of cardiac intervals. For example, SSE can instead be evaluated by $\Sigma[60/H-60/R(i)]$, while SVD can instead be evaluated by $\Sigma[60/R(i)-60/L]$. The corresponding sympathetic tone threshold (STH) and vagal tone threshold (VTH) should be changed to have the corresponding unit of time duration.

Although FIG. 8 illustrates the concept of adaptive delay of VNS modulation using two heart rate limits (H and L), it should be understood that more than one high rate limit (e.g., H1 and H2) and/or more than one low rate limit (e.g., L1 and L2) can be predefined to achieve graded control of VNS. For example, the severity of sympathetic elevation (SSE1 and SSE2) can be calculated for two different high rate threshold values (H1 and H2) and compared with two different sympathetic tone thresholds (STH1 and STH2). Correspondingly, the degree of upward modulation of VNS can be different when SSE1 exceeds STH1, compared to when SSE2 exceeds STH2. Similarly, the severity of vagal depression (SVD1 and SVD2) can be calculated for two different low rate threshold values (L1 and L2) and compared with two different vagal tone thresholds (VTH1 and VTH2). Correspondingly, the degree of downward modulation of VNS can be different when SVD1 exceeds VTH1, compared to when SVD2 exceeds VTH2.

The foregoing versions of the invention are exemplary, and are presented for purposes of illustration only. Alternative versions may include some or all of the features described herein. The invention is not limited to the foregoing versions, and rather is limited only by the claims set out below, with the invention encompassing all different versions that fall literally or equivalently within the scope of these claims.

What is claimed is:

1. An implantable pulse generator system (10) including:
   a. a nerve stimulation unit (80) configured to deliver vagal nerve stimulation pulses,
   b. an autonomic tone sensor (82) configured to generate an autonomic status signal representing a patient's autonomic status, and
   c. a control unit (62):
      (1) connected to the nerve stimulation unit (80) and the autonomic tone sensor (82), and
      (2) configured to control the nerve stimulation unit (80) to deliver vagal nerve stimulation (VNS) having intensity dependent on the autonomic status signal, the intensity of the delivered vagal nerve stimulation (VNS):
         (a) increasing along a first pathway when the autonomic status signal indicates an autonomic tone that is shifting toward greater sympathetic dominance, and
         (b) decreasing along a second pathway when the autonomic status signal indicates an autonomic tone that is shifting toward greater parasympathetic dominance,
      wherein the first and second pathways:
         i. differ, and
         ii. define a hysteresis loop.

2. The implantable pulse generator system (10) of claim 1 wherein the autonomic status signal is generated over a moving time window, whereby the autonomic status signal is dependent on the patient's autonomic status over a time period defining the window.

3. The implantable pulse generator system (10) of claim 2 wherein the autonomic status signal is generated from values of the patient's instantaneous heart rate arising during the moving time window.

4. The implantable pulse generator system (10) of claim 2 wherein the autonomic status signal is generated from values of the patient's instantaneous atrio-ventricular conduction time arising during the moving time window.

5. The implantable pulse generator system (10) of claim 2 wherein the autonomic status signal is dependent on at least one of:
   a. the average of the patient's instantaneous heart rate arising during the moving time window, and
   b. the average of the patient's instantaneous atrio-ventricular conduction time arising during the moving time window.

6. The implantable pulse generator system (10) of claim 1 wherein the control unit (62) is further configured to:
   a. increase the intensity of the delivered vagal nerve stimulation (VNS) in response to at least one of:
      (1) a decrease of the patient's heart rate, and
      (2) an increase of the patient's atrio-ventricular conduction time; and
   b. decrease the intensity of the delivered vagal nerve stimulation (VNS) in response to at least one of:
      (1) an increase of the patient's heart rate, and
      (2) a decrease of the patient's atrio-ventricular conduction time.

7. The implantable pulse generator system (10) of claim 1 wherein the control unit (62) is further configured to increase or decrease the intensity of the delivered vagal nerve stimulation (VNS) only when the autonomic status signal is within a predetermined range of values.

8. The implantable pulse generator system (10) of claim 1 wherein the control unit (62) is further configured to:
   a. increase the intensity of the delivered vagal nerve stimulation (VNS) in response to the severity of sympathetic elevation (SSE), wherein the severity of sympathetic elevation (SSE) is dependent on any degree to which the patient's heart rate exceeds a predefined high heart rate limit (H);
   b. decrease the intensity of the delivered vagal nerve stimulation (VNS) in response to the severity of vagal suppression (SVD), wherein the severity of vagal suppression (SVD) is dependent on any degree to which the patient's heart rate falls short of a predefined low heart rate limit (L).

9. The implantable pulse generator system (10) of claim 8 wherein the control unit (62) is configured to:
   a. determine the severity of sympathetic elevation (SSE) as dependent on $\Sigma[R(i)-H]$, and
   b. determine the severity of vagal depression (SVD) as dependent on $\Sigma[L-R(i)]$,
   where:
      i. i is the beat index,
      ii. R(i) is the instantaneous heart rate at the i-th beat, and
      iii. the summation is performed over all beats occurring during a moving time window.

10. The implantable pulse generator system (10) of claim 9 wherein the control unit (62) is configured to:
    a. determine the severity of sympathetic elevation (SSE) by applying a first set of predefined coefficients to the difference [R(i)-H]; and
    b. determine the severity of vagal depression (SVD) by applying a second set of predefined coefficients to the difference [L-R(i)].

11. The implantable pulse generator system (10) of claim 10 wherein the control unit (62) is configured to determine the coefficients in dependence on the patient's instantaneous heart rate.

12. The implantable pulse generator system (10) of claim 1:
   a. further including an activity sensor (68) configured to generate a metabolic demand signal, and
   b. wherein the control unit (62) is also configured to control the nerve stimulation unit (80) to deliver vagal nerve stimulation (VNS) having intensity dependent on the metabolic demand signal.

13. An implantable pulse generator system (10) including:
   a. a nerve stimulation unit (80) configured to deliver vagal nerve stimulation pulses,
   b. an autonomic tone sensor (82) configured to generate an autonomic status signal representing a patient's autonomic status, and
   c. a control unit (62):
      (1) connected to the nerve stimulation unit (80) and the autonomic tone sensor (82), and
      (2) configured to control the nerve stimulation unit (80) to deliver vagal nerve stimulation (VNS) having intensity:
         (a) dependent on the patient's autonomic status over a moving time window,
         (b) increasing along a first pathway when the patient's autonomic status indicates an autonomic tone changing toward greater sympathetic dominance, and
         (b) decreasing along a second pathway when the patient's autonomic status indicates an autonomic tone changing toward greater parasympathetic dominance,
         wherein the first and second pathways differ, and together define a hysteresis loop.

14. The implantable pulse generator system (10) of claim 13 wherein the autonomic status signal is dependent on at least one of:
   a. the average of the patient's instantaneous heart rate arising during the moving time window, and
   b. the average of the patient's instantaneous atrio-ventricular conduction time arising during the moving time window.

15. The implantable pulse generator system (10) of claim 13 wherein the control unit (62) is further configured to:
   a. increase the intensity of the delivered vagal nerve stimulation (VNS) in response to at least one of:
      (1) a decrease of the patient's heart rate, and
      (2) an increase of the patient's atrio-ventricular conduction time; and
   b. decrease the intensity of the delivered vagal nerve stimulation (VNS) in response to at least one of:
      (1) an increase of the patient's heart rate, and
      (2) a decrease of the patient's atrio-ventricular conduction time.

16. The implantable pulse generator system (10) of claim 13 wherein the control unit (62) is further configured to:
   a. increase the intensity of the delivered vagal nerve stimulation (VNS) in response to the severity of sympathetic elevation (SSE), wherein the severity of sympathetic elevation (SSE) is dependent on the application of a first set of predefined coefficients to the difference $[R(i)-H]$,
   b. decrease the intensity of the delivered vagal nerve stimulation (VNS) in response to the severity of vagal suppression (SVD), wherein the severity of vagal suppression (SVD) is dependent on the application of a second set of predefined coefficients to the difference $[L-R(i)]$,
   where:
   i. i is the beat index,
   ii. $R(i)$ is the instantaneous heart rate at the i-th beat, and
   iii. the summation is performed over all beats occurring during a moving time window.

* * * * *